US011697610B2

(12) United States Patent
Gauthier et al.

(10) Patent No.: US 11,697,610 B2
(45) Date of Patent: Jul. 11, 2023

(54) FUSED QUARTZ CONTAINER HAVING LOW LEVELS OF SURFACE DEFECTS

(71) Applicant: Momentive Performance Materials Quartz, Inc., Strongsville, OH (US)

(72) Inventors: Ben Gauthier, University Heights, OH (US); Robert Koch, Shaker Heights, OH (US); Todd Springer, Twinsburg, OH (US); David Xu, Cupertino, CA (US); Gloriana Volio, Streetsboro, OH (US)

(73) Assignee: Momentive Performance Materials Quartz, Inc., Strongsville, OH (US)

( * ) Notice: Subject to any disclaimer, the term of this patent is extended or adjusted under 35 U.S.C. 154(b) by 1044 days.

(21) Appl. No.: 16/475,156

(22) PCT Filed: Jan. 12, 2018

(86) PCT No.: PCT/US2018/013449
§ 371 (c)(1),
(2) Date: Jul. 1, 2019

(87) PCT Pub. No.: WO2018/132637
PCT Pub. Date: Jul. 19, 2018

(65) Prior Publication Data
US 2019/0330097 A1 Oct. 31, 2019

Related U.S. Application Data

(60) Provisional application No. 62/446,017, filed on Jan. 13, 2017.

(51) Int. Cl.
| C03C 3/06 | (2006.01) |
| A61B 5/154 | (2006.01) |
| A61J 1/06 | (2006.01) |
| A61L 31/02 | (2006.01) |
| A61M 5/24 | (2006.01) |
| A61M 5/31 | (2006.01) |

(Continued)

(52) U.S. Cl.
CPC ............... *C03C 3/06* (2013.01); *A61B 5/154* (2013.01); *A61J 1/065* (2013.01); *A61L 31/028* (2013.01);
(Continued)

(58) Field of Classification Search
CPC ... C03C 3/06; C03C 2201/02; C03C 2203/52; C03C 2203/10; C03C 2204/08;
(Continued)

(56) References Cited

U.S. PATENT DOCUMENTS

| 4,516,998 A | 5/1985 | Ritt et al. |
| 6,165,281 A | 12/2000 | Yoon |

(Continued)

FOREIGN PATENT DOCUMENTS

| FR | 1013074 | 7/1952 |
| IN | 1467KOL2009 A | 12/2009 |
| JP | 2010274091 | 12/2010 |

OTHER PUBLICATIONS

Sacha et. al, "Practical Fundamentals of Glass, Rubber, and Plastic Sterile Packaging Systems", Pharmaceutical Development and Technology, 2010; 15(1): p. 14-15.
(Continued)

Primary Examiner — James C Yager
(74) Attorney, Agent, or Firm — McDonald Hopkins LLC

(57) ABSTRACT

A quartz glass container is shown and described herein. The quartz glass container exhibits a low concentration of surface defects on an inner surface of the container. In aspects hereof, the container may have a surface defect density of 50 or fewer surface defects per square centimeter within a 1 cm band centered 1 cm from the base of the container.

11 Claims, 4 Drawing Sheets

(51) Int. Cl.
*C03B 23/09* (2006.01)
*C03B 23/11* (2006.01)

(52) U.S. Cl.
CPC ............ *A61M 5/24* (2013.01); *A61M 5/3129* (2013.01); *C03B 23/092* (2013.01); *C03B 23/11* (2013.01); *C03B 2201/02* (2013.01); *C03C 2201/02* (2013.01); *C03C 2203/52* (2013.01); *Y10T 428/13* (2015.01); *Y10T 428/131* (2015.01)

(58) Field of Classification Search
CPC ......... A61B 5/154; A61J 1/065; A61J 1/1468; A61L 31/028; A61M 5/24; A61M 5/3129; C03B 23/092; C03B 23/11; C03B 2201/02; Y10T 428/13; Y10T 428/131
See application file for complete search history.

(56) References Cited

U.S. PATENT DOCUMENTS

| | | |
|---|---|---|
| 7,980,096 B2 | 7/2011 | Bartsch |
| 8,820,119 B2 | 9/2014 | Kuwabara et al. |
| 2009/0099000 A1 | 4/2009 | Kuwabara et al. |
| 2012/0148770 A1 | 6/2012 | Rong et al. |
| 2014/0151499 A1 | 6/2014 | Mellor et al. |
| 2015/0218047 A1 | 8/2015 | Xu et al. |
| 2016/0130170 A1 | 5/2016 | Maennl et al. |
| 2016/0145150 A1 | 5/2016 | Bookbinder et al. |

OTHER PUBLICATIONS

Zhao et. al, "Glass Delamination: A Comparison of the Inner Surface Performance of Vials and Pre-filled syringes", AAPS PharmaSciTech, vol. 15, No. 6, Dec. 2014.

Iacocca et al, "Corrosive Attack of Glass by a Pharmaceutical Compound", J. Mater Sci. 2007, vol. 42, pp. 801-811.

Wen et Al, "Nondestructive Detection of Glass Vial Inner Surface Morphology with Differential Interference Contrast Microscopy", J. of Pharm. Sci., vol. 101, No. 4, Apr. 2012, p. 1380.

Sangra, "A Review of Glass Types Available for Packaging", Journal of the Parenteral Drug Association, Mar.-pr., 1979, vol. 33, No. 2, pp. 61-67.

Patent Cooperation Treaty (PCT), International Search Report and Written Opinion for Application PCT/US2018/013449 filed Jan. 12, 2018, dated May 4, 2018, International Searching Authority, EP.

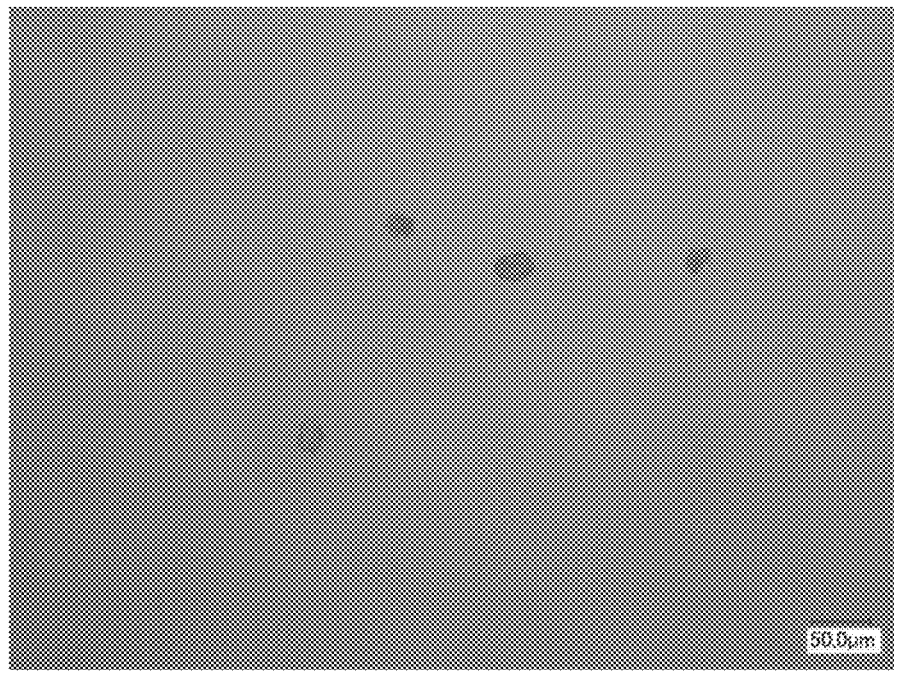
Figure 2. (fused quartz article after conventional fabrication)
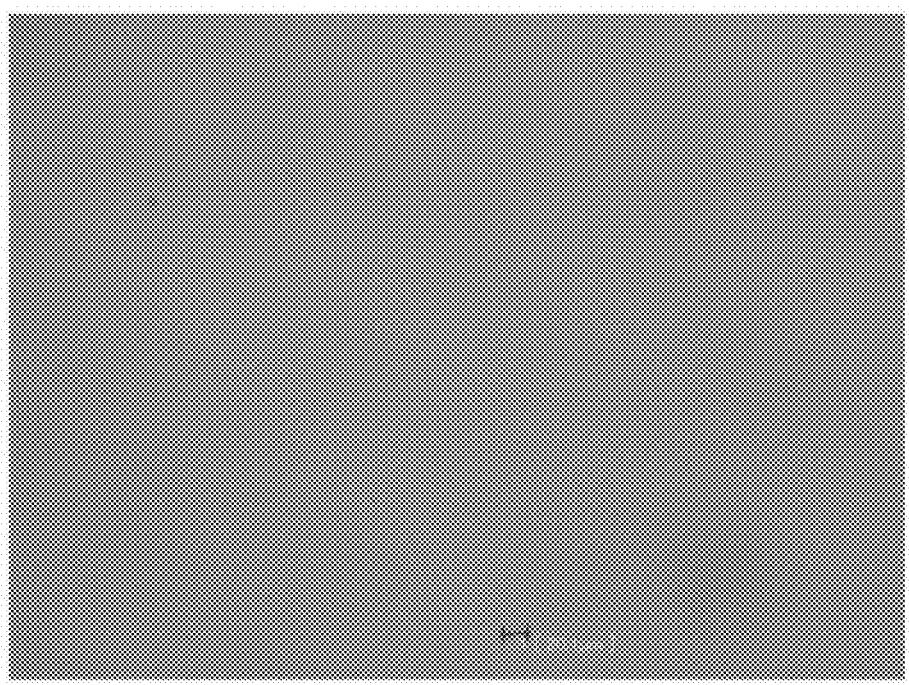
Figure 3. (fused quartz article, current invention)

FUSED QUARTZ CONTAINER HAVING LOW LEVELS OF SURFACE DEFECTS

CROSS-REFERENCE TO RELATED APPLICATIONS

The present application is a 35 U.S.C. 371 national stage filing of PCT Application No. PCT/US2018/013449 filed Jan. 12, 2018, which claims priority to and the benefit of U.S. Provisional Application No. 62/446,017 filed on Jan. 13, 2017, the entire disclosure of which is incorporated herein by reference.

FIELD OF INVENTION

The present invention relates to fused quartz glass containers. In particular, provided is a fused quartz glass container having a low concentration of surface features, such as those that may arise from the redeposit of glass or glass constituents during the manufacturing process. Also shown and described is a method of making such containers.

BACKGROUND

Glass materials are often used in pharmaceutical packaging. There has been a recent trend in the pharmaceutical market toward the increased use of biological (protein-based) drugs that are more "sensitive" than traditional drugs. With these types of drugs, the topic of drug/container interaction becomes increasingly important due to the lower stability of these drugs and their propensity to degrade during storage, especially when formulated as a liquid. Because of this, extractable substances (e.g. dissolved cations) coming from the pharmaceutical packaging container can cause issues with regard to efficacy and purity of these drugs (including drug instability, toxicity, etc). *A Review of Glass Types Available for Packaging*, S. V. Sangra, Journal of the Parenteral Drug Association, March-pr., 1979, Vol. 33, No. 2, pp. 61-67.

Cationic extraction from traditional glasses used in pharmaceutical packaging can create issues with the purity and/or effectiveness of such protein-based drugs. The mechanism of cationic extraction is typically hydronium/alkali ion exchange that causes a pH increase, which is then followed by bulk dissolution, especially in Type I (e.g., borosilicate glass, such as Schott Fiolax®) and Type II (treated soda-lime silicate) glasses. The poor chemical durability of these glasses arises from the fact that soluble cations, such as $Na^+$, $Li^+$, $K^+$, $Mg^{2+}$, $Ca^{2+}$ and/or $Ba^{2+}$ are used to flux these glasses to achieve a suitably low working point temperature that makes them highly processable with standard glass melting equipment (see, e.g., U.S. Pat. Nos. 5,782,815 and 6,027,481).

Glass particle generation due to delamination is one of the major concerns in pharmaceutical packaging industries when Type I and Type II glasses are used as the container for pharmaceutical products. Delamination occurs when top layers of a glass separate at a scale that is barely visible or invisible to the naked eyes as shown in FIG. 1 of Ronald G Iacocca, "The Cause and Implications of Glass Delamination," Pharmaceutical Technology, 2011, pp s6-s9, the disclosure of which is incorporated herein by reference in its entirety. The delamination particles become suspended in drug solutions, posing a serious risk to the consumer.

Glasses without chemical modifiers (e.g., alkali metals, borates, alkaline earth metals) such as fused quartz glass are preferable from a chemical purity (low extractables) and chemical durability perspective, but it was previously believed such glasses may be difficult to manufacture due to the high processing temperatures required (typically >2,000° C.). Even when fused quartz glasses can be melted and formed into tubing, it is then often difficult to flame convert them into pharmaceutical packages (vials, syringe barrels, ampoules, etc), due to a high working point temperature (>1,700° C.). Thus, such glasses have generally not been used to manufacture pharmaceutical packaging. U.S. Pat. Nos. 6,200,658 and 6,537,626 show that efforts have been made to coat the interior surfaces of traditional glass containers with a layer of silica to reduce extractables (e.g., Schott Type I plus®) and glass particles that are produced through delamination. Providing coated articles, however, is cumbersome, expensive, and difficult to ascertain the integrity of the coating. For these reasons such articles are not widely accepted in the pharmaceutical packaging market.

Glass packaging containers can also contain surface defects and/or irregularities created from the glass formation process itself. One such example is the presence of redeposited adhered glass particles such as addressed in U.S. Pat. No. 6,165,281. The '281 patent describes minute broken glass particles (3-60 micron and above) generated during a commonly practiced "cutting off" process involving flames to segment glass tubes at appropriate lengths. Said particles scatter along the inner wall and then become adhered during a subsequent heat treatment. Sacha et al ("Practical Fundamentals of Glass, Rubber, and Plastic Sterile Packaging Systems", Pharmaceutical Development and Technology, 2010; 15(1): pg. 14-15) discusses rough spots formed on the inner surface of a vial as a result of redeposited glass that was vaporized during the heating/forming process. In these cases, the redeposited glass could be chemically different from the bulk of the container, and can be more reactive and less durable.

Inner surface glass particles are generally present throughout the industry, but to date, it appears that attention is only paid to particles greater than approximately 0.2 mm (200 micron). The pharmaceutical vial tubing specification from Corning Pharmaceutical Glass, LLC, for example, considers the presence of glass particles sufficient to reject the tube when either any particles greater than 0.5 mm (500 micron) are identified or when more than 5-10 particles greater than 0.2 mm is identified (exact threshold depending on outer diameter of the tubing). (See http://www.corning.com/media/worldwide/cpt/documents/Specs_Vialtubing.) Particles less than 0.2 mm are not considered as a rejectable criteria. Similarly, the Stevanato Group, which makes glass forming equipment and glass packaging for the pharmaceutical industry, (http://www.ondrugdelivery.com/publications/Prefilled%20 Syringes%202009/SPAMI%20Andrea%20Sardella.pdf, retrieved Dec. 1, 2016), discusses the challenge of glass tubing specifications that allow up to 9 particles in the 0.20-25 mm range, while the requirements of the pharmaceutical industry (in this case the current Japanese Quality Requirement) do not allow any defects greater than 0.3 mm. Likewise, particles less than 0.2 mm are not addressed. U.S. Patent Application Publication 2009/0099000 discusses the industry challenge of deteriorated regions of the inner surface that result from alkali-containing materials either exuded from or vaporized from the glass that condense and redeposit, especially during the bottom forming.

As discussed above, there is significant concern in the industry for glass delamination, where high aspect ratio glass "flakes" separate from the bulk and enter into the parenteral solution. Generally, the glass delamination particles or flakes are distinct from redeposited glass particles and features resulting from redeposit of volatile glass constituents. U.S. Patent Application Publication No. 2014/0150499 expresses concern for delamination flakes, and differentiates them from what they refer to as "tramp particles" based on the aspect ratio, with the former having aspect ratios typically greater than 50 and the later having aspect ratios less than about 3. Based on the context of this reference, "tramp particles" appears to include both redeposited glass and others such as particles that precipitate directly from the parenteral solution.

In a paper by Zhao et. al ("Glass Delamination: A Comparison of the Inner Surface Performance of Vials and Prefilled Syringes," AAPS PharmaSciTech, Vol 15, No 6, December 2014), the authors discuss the observation of raised, sodium rich regions of the glass, and attribute this to nucleation of gas bubbles during the cooling of the glass (reboil). These types of features, considered "features resulting from redeposit of volatile glass constituents," are also discussed in a paper by Iacocca et al ("Corrosive Attack of Glass by a Pharmaceutical Compound," J. Mater. Sci. (2007), 42:803), where they are described as crater-like, with the cause attributed to reboil. In a paper by Wen et. al ("Nondestructive Detection of Glass Vial Inner Surface Morphology with Differential Interference Contrast Microscopy," J. of Pharm. Sci., Vol 101, No. 4 April 2012, page 1380), the authors discuss pitting or craters as regions of phase separation (specifically rich in sodium and boron ions), more prevalent in high alkalinity vials because of vaporization of alkali sodium and borate ions depositing on the surface as a result of the high temperatures required to form the vial bottoms. Other features that may have the shape of particles, but not be sufficiently amorphous to be categorized as glass, may also fall under this category of "features resulting from the redeposit of volatile glass constituents".

Depending on the composition, morphology, and degree of adhesion of adhered glass particles, the presence of such particles could be detrimental to the end use application for a number of reasons. They may break free of the surface and contaminate the product, serve as a site for protein aggregation which could affect the efficacy of the drug formulation, or simply alter the chemical durability of the container and thereby increase the levels of extractables at the surface. Similar issues could arise from other types of features that resulted from redeposit of volatile glass constituents. Previous efforts in the industry have focused on traditional multi-component glass such as soda lime silicate, borosilicate, and alumino silicate glasses. These are well known in the pharmaceutical glass industry. The challenge with these types of glasses is that there is unavoidably at least one component that is more volatile than others that results in the majority of the redeposited particles. A wide range of approaches has been proposed to help reduce the severity of the redeposited particles, but only to limited effect. U.S. Pat. No. 6,165,281 discusses using a brush to remove them from conventional vials. U.S. Pat. No. 7,980,096 discusses using a purge gas and/or plugging the end of the vertically oriented glass tubing used in conventional vials in order to reduce them. U.S. Pat. No. 4,516,998 also mentions a purge/overpressure inside of the conventional tubing. U.S. Pat. No. 8,820,119 discusses a method to fire blast the interior surface of conventional vials in order to restore a pristine surface.

While particle removal techniques (e.g., U.S. Pat. No. 6,165,281) and intricate inspection devices and quality procedures have been incorporated to attempt to limit the problem, there remains a yet unsolved problem of creating packaging containers that are substantially free of redeposited glass, particularly for the smallest particles in less than 200 micron range. This is particularly important on high-throughput equipment, suitable for the pharmaceutical packaging industry, which produces greater than 50, greater than 200, or even greater than 2000 parts an hour.

SUMMARY

The following presents a summary of this disclosure to provide a basic understanding of some aspects. This summary is intended to neither identify key or critical elements nor define any limitations of embodiments or claims. Furthermore, this summary may provide a simplified overview of some aspects that may be described in greater detail in other portions of this disclosure.

In one aspect, the present invention provides a fused quartz glass container having a low concentration of surface features. Included in this count are features that arise from the redeposit of volatile glass constituents including, redeposited glass particles, non-glass particles and other craters or features that result from the redeposit of volatile glass constituents. In embodiments, the fused quartz glass container may have a surface feature density of 50 or fewer, even down to 5 or fewer, redeposited glass particles per square centimeter.

In one aspect, the present disclosure provides a quartz glass pharmaceutical container defining an interior volume and having an upper end, a base end, at least one wall defining an inner surface and an outer surface, wherein the inner surface of the container has a surface feature density of 50 or fewer surface features per square centimeter within a 1 cm band centered 1 cm from the base end of the pharmaceutical container, the surface features having a size of 1 to 200 μm.

In one embodiment of the quartz glass pharmaceutical container, the surface feature density is 10 or fewer redeposited features per square centimeter.

In one embodiment of the quartz glass pharmaceutical container, the surface feature density is 5 or fewer redeposited features per square centimeter.

In one embodiment of the quartz glass pharmaceutical container according to any previous embodiment, wherein the surface features have a size of 10 to 200 μm.

In one embodiment of the quartz glass pharmaceutical container according to any previous embodiment, the surface features have a size of from about 10 μm to about 200 μm; from about 20 μm to about 150 μm; from about 50 to about 100 μm; from greater than 10 μm to about 50 μm, from greater than 10 μm to about 100 μm; or 1 μm to about 10 μm.

In one embodiment of the quartz glass pharmaceutical container according to any previous embodiment, the surface feature density is 5 or fewer features of 50 micron or greater per square centimeter.

In one embodiment of the quartz glass pharmaceutical container according to any previous embodiment, the surface feature density is 5 or fewer features of 10 micron or greater per square centimeter.

In one embodiment of the quartz glass pharmaceutical container according to any previous embodiment, the surface features have a two-dimensional aspect ratio of 50 or less.

In one embodiment of the quartz glass pharmaceutical container according to any previous embodiment, the surface features have a two-dimensional aspect ratio of less than 20, less then 10, less than 5, less than 2, or about 1.

In one embodiment of the quartz glass pharmaceutical container according to any previous embodiment, the container has a surface feature density of:

50 or fewer surface features in the size range of 10-200 μm or greater per square centimeter;

40 or fewer surface features in the size range of 10-200 μm or greater per square centimeter;

30 or fewer surface features in the size range of 10-200 μm or greater per square centimeter;

20 or fewer surface features in the size range of 10-200 μm per square centimeter;

10 or fewer surface features in the size range of 10-200 μm or greater per square centimeter; or 5 or fewer surface features in the size range of 10-200 μm or greater per square centimeter. Here as elsewhere in the specification and claims, ranges can be combined to form new and non-specified ranges.

In one embodiment of the quartz glass pharmaceutical container according to any previous embodiment, the container has a surface feature density of:

50 or fewer surface features of 1-10 μm per square centimeter;

40 or fewer surface features of 1-10 μm or greater per square centimeter;

30 or fewer surface features of 1-10 μm or greater per square centimeter;

20 or fewer surface features of 1-10 μm or greater per square centimeter;

10 or fewer surface features of 1-10 μm or greater per square centimeter; or 5 or fewer surface features of 1-10 μm or greater per square centimeter.

In one embodiment of the quartz glass pharmaceutical container according to any previous embodiment, the container has a $SiO_2$ content of 99.99 wt. % or greater, 99.999 wt. % or greater; about 99.9 wt. % to about 99.9999 wt. %; about 99.9 wt. % to about 99.9995 wt. %; about 99.9 wt. % to about 99.999 wt. %; or about 99.99 wt. % to about 99.995 wt. %.

In one embodiment of the quartz glass pharmaceutical container according to any previous embodiment, the quartz glass container is chosen from a vial, a tube, a vacuum sealed tube (e.g., Vacutainer® type tubes), a cartridge, a syringe, a syringe barrel, or an ampoule.

In one embodiment of the quartz glass pharmaceutical container according to any previous embodiment, the container comprises a pharmaceutical fluid disposed in the container.

In another aspect, the present description provides a process for forming a plurality of quartz glass containers comprising: providing a quartz glass tube having a first open end and second open end opposite the first open end; forming one or more features of a container at the first open end; forming one or more features of a container at the second open end; separating the quartz glass tube at a point distal to each of the first and second open ends, the separating operation providing two containers and forming a bottom of each container.

In one embodiment, the process for forming a pluarlity of quartz glass containers, the quartz glass tube is oriented horizontally, vertically, or at an angle between the horizontal and vertical.

In one embodiment of the process according to any previous embodiment, the process comprising purging the tube with a gas during the step of (i) forming one or more features of a container at the first open end, (ii) forming one or more features of a container at the second open end, or both (i) and (ii). In one embodiment, the gas is an inert gas.

In one embodiment of the process according to any previous embodiment, the process is operated to process 50 to 3000 quartz glass tubes per hour.

In still another aspect, provided is a pharmaceutical packaging container made from the process of according to any previous embodiment or aspect. In one embodiment, the container defines an interior volume and has an upper end, a base end, and at least one wall defining an inner surface and an outer surface, wherein the inner surface of the container has a surface feature density of 50 or fewer surface features per square centimeter within a 1 cm band centered 1 cm from the base end of the container.

The following description and the drawings disclose various illustrative aspects. Some improvements and novel aspects may be expressly identified, while others may be apparent from the description and drawings.

BRIEF DESCRIPTION OF THE DRAWINGS

The accompanying drawings illustrate various systems, apparatuses, devices and related methods, in which like reference characters refer to like parts throughout, and in which:

FIG. 2 is a photograph of a microscopic image of a glass surface having surface features derived from the redeposit of volatile glass constituents;

FIG. 3 is a photograph of a microscopic image of a glass surface in accordance with aspects of the present technology;

DETAILED DESCRIPTION

Figure 1:
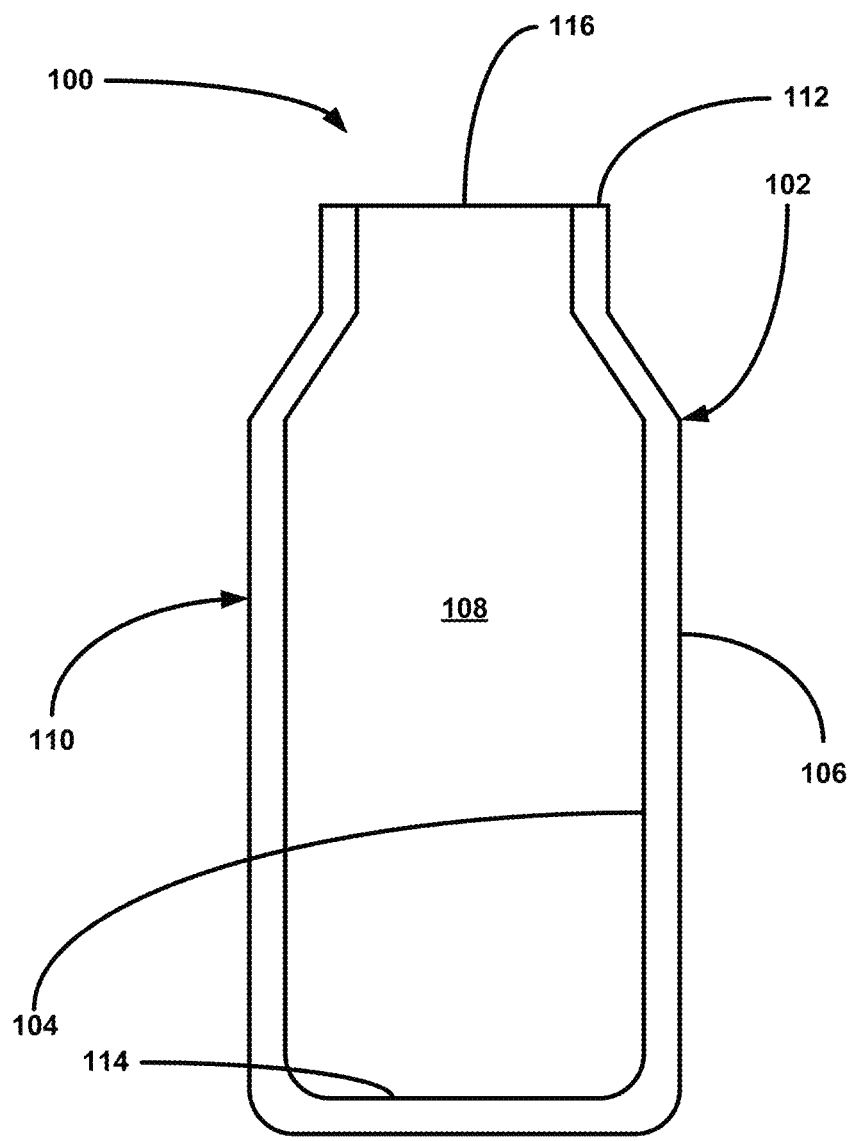
FIG. 1 is a cross-sectional view of a glass container.

Reference will now be made to exemplary embodiments, examples of which are illustrated in the accompanying drawings. It is to be understood that other embodiments may be utilized and structural and functional changes may be made. Moreover, features of the various embodiments may be combined or altered. As such, the following description is presented by way of illustration only and should not limit in any way the various alternatives and modifications that may be made to the illustrated embodiments. In this disclosure, numerous specific details provide a thorough understanding of the subject disclosure. It should be understood that aspects of this disclosure may be practiced with other embodiments not necessarily including all aspects described herein, etc.

As used herein, the words "example" and "exemplary" means an instance, or illustration. The words "example" or "exemplary" do not indicate a key or preferred aspect or embodiment. The word "or" is intended to be inclusive rather than exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

Provided is a fused quartz glass container having low levels of surface defects on an inner surface of the container. As used herein, the term "surface features," "redeposit features," "surface defect," "redeposit defect," and "redeposit features of volatile glass particles" may be used interchangeably and refer to a surface feature arising from the redeposit or adherence of particulate matter on the inner surface of the container. The surface defects may typically arise from the manufacture of the glass article. They can be derived from redeposit of a volatilized or evaporated glass constituent during the manufacture of a glass article. They can also be derived from the adherence of glass particles that are not volatilized or evaporated material, but rather are particles or pieces that are produced during cutting or forming operations on the container during manufacture. The surface features may include glass particles, redeposited glass particles, adhered glass particles, redeposited particles that are not in a glass phase, pits, depressions, and craters, non-glass particles or other features (e.g. texture, rings, etc.) that resulted from the redeposit of volatile glass constituents. Pits, craters, and depressions may be considered as regions or voids where material has been removed from and is missing from a region of the quartz glass, and may result from material being volatilized from the glass surface itself.

The surface features or defects are those features having a size (as determined by the largest dimension (e.g., length or width) of the feature) of greater than 1 μm and less than 200 μm. In embodiments, the redeposited glass particles may have a size of from about 1 μm to 200 μm; from about 10 μm to about 200 μm; from about 20 μm to about 150 μm; even from about 50 to about 100 μm. In still other embodiments, the surface features have a size of from greater than 10 μm to about 50 μm, or from greater than 10 μm to about 100 μm. In one embodiment, the surface features of volatile glass constituents are those having a size of 1 μm to about 10 μm. Here as elsewhere in the specification and claims, numerical values may be combined to form new and non-specified ranges. Moreover, the surface features have a two-dimensional aspect ratio (ratio of length to width of the feature) of less than 50, less than 20, less then 10, less than 5, less than 2, and even about 1. The two-dimensional aspect ratio is evaluated because the three dimensional shape of the feature may not be completely ascertainable when evaluating them through a microscope.

The surface features are distinguished from delamination flakes. Delamination refers to a phenomenon in which glass particles are released from the surface of the glass during or after usage of the vial such as by storage of a fluid within the container. Delamination may arise from normal usage (e.g., movement of the fluid during transport, shipping, handling, etc.) or through a series of leaching, corrosion, and/or weathering reactions, and may or may not be observable prior to release. Redeposited glass particles, on the other hand, are observable with sufficient magnification before any particular exposure or reactions are applied to the glass. In general, the delamination glass particles are silica-rich flakes of glass that originate from the interior surface of the package as a result of the leaching of modifier ions into a solution contained within the package. These flakes may generally be from about 1 nm to about 2 μm thick with a width greater than about 50 μm. These flakes are primarily composed of silica, and generally do not further degrade after being released from the surface of the glass. Delamination produces particulate flakes or lamellae that are irregularly shaped and typically have a maximum length greater than about 50 μm but often greater than about 200 μm. The thickness of the flakes is usually greater than about 100 nm and may be as large as about 1 μm. Thus, the minimum aspect ratio of the flakes is typically greater than about 50. The aspect ratio may be greater than about 100 and sometimes greater than about 1000. Moreover, the redeposited features of volatile glass constituents, if present, are observable through microscopic analysis as discussed further herein. Delamination flakes, however, are typically not evidenced via microscopic analysis until the container is exposed to a fluid resulting in delamination of the glass material.

Although the terms may be used to denote compositions or articles of different materials (different silica concentrations), as used herein, the term "quartz" may be used interchangeably with "quartz glass" or "fused quartz," referring to a composition, a part, a product, or an article formed from a mixture comprising natural or synthetic sand (silica). As used herein, the term "quartz" also includes and may be used interchangeably with quartz glass, fused quartz, fused silica, amorphous silica, and vitreous silica. Either or both natural or synthetic sand (silica) can be used in the composition of the invention, and the term is used to denote compositions comprising either naturally occurring crystalline silica such as sand/rock, synthetically derived silicon dioxide (silica), or a mixture of both. The term "sand" may be used interchangeably with silica, denoting either natural sand or synthetic sand, or a mixture of both.

The fused quartz containers comprise high purity silica. The silica in the fused quartz container has a silica content of 99.9 wt. % or greater. In still other embodiments, the glass compositions and articles formed therefrom have a $SiO_2$ content of 99.99 wt. % or greater, 99.999 wt. % or greater. In further embodiments, the glass composition can have a $SiO_2$ content of about 99.9 wt. % to about 99.9999 wt. %, about 99.9 wt. % to about 99.9995 wt. %, about 99.9 wt. % to about 99.999 wt. %, even about 99.99 wt. % to about 99.995 wt. %. Here as elsewhere in the specification and claims, ranges can be combined to form new and non-specified ranges.

An example of a fused quartz glass container is illustrated in FIG. 1. The glass container 100 comprises a glass body 102 defining an inner surface 104 and an outer surface 106 and generally defines an interior volume 108. The container is shaped to define one or more walls 110, an upper end 112, and a base 114. The upper end 112 may define an opening 116 through which liquids stored within the container may exit the container. The opening may be configured to be covered by a cap, plug, lid, etc., or it may contain a frangible covering that may be broken to expose the opening.

The container may be shaped as desired for a particular purpose or intended application. While the container may be substantially circular in circumference (and define a single unitary wall 110 having no defined edges or corners), the circumference of the container may define any shape (e.g., square, rectangular, hexagonal, etc.) and may thus define a plurality of walls 110 with adjacent walls meeting at an edge or corner. While the glass container 100 is depicted in FIG. 1 as having a specific shape form (i.e., a vial), it should be understood that the glass container 100 may have other shape forms, including, but not limited to, cartridges, syringes, syringe barrels, ampoules, bottles, flasks, phials, tubes, vacuum sealed tubes, beakers, or the like.

In accordance with the present technology, the containers have a low concentration of surface features (density of surface features of volatile glass constituents) on the inner surface of the container. In order to simplify the analysis and exaggerate differences, as used herein, the density of surface features refers to the number of surface features on the inner surface of the container wall specifically within an approximately 1 cm wide band located in the vicinity where such features are considered prominent. The band is 1 cm wide and follows the entire circumference, such that the area of the band is equal to $A_b=1$ [cm]*$\pi$*d[cm], where d refers to the inner diameter of the band. The location of this band on an axisymetric or axially oriented part is such that the center line of the band is located 1 cm up from the base of the container. The present glass containers have a surface feature density of 50 or fewer redeposited surface features per square centimeter; 40 or fewer surface features per square centimeter; 30 or fewer surface features per square centimeter; 20 or fewer surface features per square centimeter; 10 or fewer surface features per square centimeter; even 5 or fewer surface features per square centimeter.

In one embodiment, the container has a surface feature density of 50 or fewer surface features in the size range of 10-200 µm or greater per square centimeter; 40 or fewer surface features in the size range of 10-200 µm or greater per square centimeter; 30 or fewer surface features in the size range of 10-200 µm or greater per square centimeter; 20 or fewer surface features in the size range of 10-200 µm per square centimeter; 10 or fewer surface features in the size range of 10-200 µm or greater per square centimeter; even 5 or fewer surface features in the size range of 10-200 µm or greater per square centimeter. Here as elsewhere in the specification and claims, ranges can be combined to form new and non-specified ranges.

In one embodiment, the container has a surface feature density of 50 or fewer surface features of 1-10 µm per square centimeter; 40 or fewer surface features of 1-10 µm or greater per square centimeter; 30 or fewer surface features of 1-10 µm or greater per square centimeter; 20 or fewer surface features of 1-10 µm or greater per square centimeter; 10 or fewer surface features of 1-10 µm or greater per square centimeter; even 5 or fewer surface features of 1-10 µm or greater per square centimeter. Here as elsewhere in the specification and claims, ranges can be combined to form new and non-specified ranges.

The surface feature density is evaluated using an optical microscope on an intact container. The microscopy is conducted through the wall by focusing on the inner surface of the container. Imaging is conducted on a 1 cm band centered 1 cm up from the base of the vial. Imaging may be conducted using any suitable optical microscope. In one embodiment, imaging is performed with a Keyence optical microscope at a magnification of 450x; and a camera having a field of view of approximately 575 micron by 775 micron. Imaging is done at five random areas located within the 1 cm band. In each image, the number of surface features that had a dimension length of greater than approximately 10 µm is counted.

Also provided is a method for manufacturing fused quartz glass containers having low concentrations of surface features. The method is fully automatable and may allow for high throughput production of fused glass containers having a low concentration of redeposited features of volatile glass constituents.

The method begins by forming desired external features of the container such as, for example, the mouth, crown, neck, shoulder, etc., on one end of a glass tube. The method disclosed relies on equipment that is configured in order to allow the following steps to take place. First, a glass tube is automatically transferred into a rotating chuck on either an index forming or continuous forming machine. The machine then begins by forming desired external features of the container, such as, for example, the mouth, crown, neck, shoulder, etc. on one end of the glass tube. The formation of the external features may be performed in a manner similar to conventional forming techniques, whereby the glass is heated up, and the shape is crafted by pressing with suitable tooling on both the inner diameter and the outer diameter. In accordance with the present method, these features are formed onto a shorter segment than in a conventional forming method, and the length of the tube is approximately twice as long as necessary to produce one vial. Once the desired features are formed, the tube is reversed in orientation such that the end that has not yet been worked is facing outward. This can be done by either extracting, flipping, and returning the part into the chuck, or alternatively, in the process of passing the tube from one chuck to another. Similar features are then formed on the opposite end of the tube using similar processing steps, to result in a double-headed container. During formation of the features at either end of the tube, the quartz tube may be purged by application of a gas to the tube. In an embodiment, the gas is a clean gas and flow rate of the gas may be selected as desired. A clean gas may be understood as a gas that is free of or substantially free of solid particulates and/or liquid and/or gaseous contaminates that could potentially lead to particulate or residue generation. In one embodiment, the clean gas is an inert gas. Suitable gases include, but are not limited to, air, helium, nitrogen, argon, carbon dioxide, methane, etc., or a combination of two or more thereof. This double headed container is then separated in two during a single bottom forming step using a flame. Careful control of both torch heating, as well as rotational control on each end of the tube result in a pair of consistently formed bottoms and two newly separated parts. Thus, two vials are formed from a single bottom forming step without the need to puncture a solid base or near solid base to form the opening for the new mouth as is the case in conventional approaches. This process can be practiced in either the vertical orientation, the horizontal orientation, or even in an orientation between the two (angled). The invention can also be used with purge and/or plugging approaches as well.

Further, with a sufficient degree of automation that is familiar to one skilled in the art, the process allows for high throughput process and can process greater than 50 pieces per hour; greater than 75 pieces per hour; greater than 100 pieces per hour; greater than 250 pieces per hour; greater than 500 pieces per hour; greater than 1000 pieces per hour; greater than about 2000 pieces per hour; even up to about 3000 pieces per hour. Further, with a sufficient degree of automation that is familiar to one skilled in the art, the process allows for high throughput process and can process greater than 50 pieces per hour; greater than 75 pieces per hour; greater than 100 pieces per hour; greater than 250 pieces per hour; greater than 500 pieces per hour; greater than 1000 pieces per hour; greater than about 2000 pieces per hour; even up to about 3000 pieces per hour.

The method can be implemented on one or more of various styles of automatic forming equipment used in tubular glass container manufacturing. As would be known in the art, such equipment typically includes, but is not limited to glass and container-transferring equipment, which can incorporate vacuum, pneumatic, hydraulic, robotic and/or servo-driven pick and place tooling and conveyors. Additionally, the equipment is often configured with rotating chucks that 1) grip glass tubes, 2) rotate to ensure symmetric heating and fabrication, and 3) can carry glass tubes through one or more sequences of fabrication steps. Carrying can be performed in a stop/start or indexing fashion (index forming), where fabrication steps are performed at discrete locations and the index motions take place at a prescribed frequency. Alternatively, carrying can be performed in a continuously rotating fashion, where tooling can travel alongside the traveling glass as fabrication steps take place (continuous forming). In both cases, the intention is to produce highly reproducible parts at high fabrication rates with minimal operator interaction. Automatic equipment may also employ pneumatic, hydraulic, spring or servo-motor driven tooling in order to apply pressure to shape the glass, as well as gas burners to heat the glass. Such burners may or may not have flow control devices for controlling one or more of fuel and oxidizer flow.

What has been described above includes examples of the present specification. It is, of course, not possible to describe every conceivable combination of components or methodologies for purposes of describing the present specification, but one of ordinary skill in the art may recognize that many further combinations and permutations of the present specification are possible. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

EXAMPLES

A fused quartz glass article was prepared in a conventional manner by one skilled in the art, without incorporating any of the steps outlined herein to avoid glass constituent redeposit. Shown in FIG. 2 is an example region of said article showing four adhered glass particles greater than 10 μm in length. With the frame of the picture capturing approximately 0.0045 cm$^2$, this would represent approximately 900 particles per square cm. This is compared with an article made incorporating the steps outlined herein where no such particles are seen (Shown in FIG. 3). A selection of Type I borosilicate vials were assembled representing industry benchmarks for larger volume vials (20 ml and 50 ml). These were made by three different manufacturers located in the US and Europe. These were examined "as manufactured", with none of them having received ammonium or other post-process treatment. While details of manufacturing operations are proprietary to each manufacturer, it is expected that each of these has passed an inspection criteria meant to sort out defective products. Larger vial sizes (20 and 50 ml) were selected intentionally as it is understood in the industry that redeposited particles are especially challenging for the larger vials as they require more heat to form. Thus this size selection is expected to amplify the number of surface features present.

50 ml Fused quartz glass vials are prepared as follows: 1) clean quartz glass tubing of 40 mm outer diameter and approximately 160-180 mm in length, open on both ends, is fed into automated vial forming equipment. 2) Geometric features related to the mouth, crown, neck and shoulder are formed on one of the two open ends in an automated, controlled fashion, applying heat by means of torches and pressing the glass with glass-working tooling whilst the tube is being rotated about its axis, while a centerline inert gas purge is being applied. 3) A similar process is repeated on the other open end located on the opposite side of the tube. 4) A separation step is performed using torch applied heat and controlled pulling and pressing whilst the tube is being rotated about its axis. This separation step also results in the formation of bottoms for both pieces. At this point the pieces demonstrate that they have a greatly reduced number of redeposited glass particles (or preferably and more typically no such particles). The articles then pass through an outer surface cleaning process, which while has no impact on the inner surface of the glass, does make the outer surface of the glass easier to see through.

Vials were examined in their whole state (un-cut), using a Keyence optical microscope at a magnification of 450×. The vials were preserved intact, and the microscopy was done through-the-wall by focusing on the inner surface in order to avoid possible sample contamination/altering during sectioning. The focal plane of the inner surface was validating to ensure that it corresponded to the correct wall thickness. The field of view of the camera used with the microscope was approximately 575 micron by 775 micron area.

Each of the borosilicate vials had regions near the base with surface features in the 5-50 micron range, although in many cases the smallest of those (<10 micron) were much too frequent to count and difficult to resolve anyway. Thus, only particles >10 microns were counted, as these were more clearly correlated with previous literature. This greatly reduced the amount of image analysis as over 90% of the particles were smaller than this cut off length.

At least 5 microscope images/areas were selected for each sample vial (at least 10 for each fused quartz vial). The imaging areas were located in random locations within a 1 cm band centered 1 cm up from the base of the vial. Each of these images represents about 0.3% of the area contained within the band. In each image, the number of redeposited glass particles or features resulting from redeposited volatile glass constituents that had a length dimension of greater than approximately 10 micron were counted. The number of particles greater than 10 micron per image ranged from 0 (most common) up to 39 (less common). Interestingly, many of the images with 0 particles in this size category did not contain any discernable particles or features of interest, while some contained an enormous amount of features in the <10 micron range. No features of this type were observed in any of this particular set of fused quartz vials, even after examining about twice as many locations as the other vials.

The three borosilicate vial types had relevant densities of approximately 9, 23 and 12 particles greater than 10 microns per square mm (907, 2308, and 1222 particles greater than 10 microns per square cm respectively) within the specified 1 cm band. Since no features were found on the fused quartz vial during this testing, a single fictitious particle is used in calculations to result in a density of less than 0.04 particles greater than 10 microns per square mm (<4 particles per square cm) within the same 1 cm band. This represents a >99.4% reduction (greater than 2 orders of magnitude) in the frequency of such features in this region.

In addition to the images counted above, a course evaluation of approximately 1% (2% in the case of the fused quartz) of the remainder of the vial inner body inner surface was performed to look for evidence of larger particles (>50 microns) in other regions of the vial outside of this band. Here the borosilicate vials had 2, 1 and 0 such particles per vial respectively, while no such particles were found on the fused quartz vials.

| | Vial Size (ml) | Samples analyzed # | Area analyzed (cm²) | Particles* (count) | Area density (particles*/cm²) |
|---|---|---|---|---|---|
| Vendor A, Type I Borosilicate | 50 | 4 | 0.11 | 97 | 907 |
| Vendor B, Type I Borosilicate | 50 | 5 | 0.12 | 288 | 2308 |
| Vendor C, Type I Borosilicate | 20 | 5 | 0.12 | 147 | 1222 |
| Fused Quartz, current invention | 50 | 5 | 0.22 | 0 | (less than 4) |

*Particles definition used here includes redeposited glass particles and features resulting from the redeposit of volatile glass consituents with a linear dimension of greater than 10 microns.

Comparative Example

Quartz Glass Tube

Figure 4:
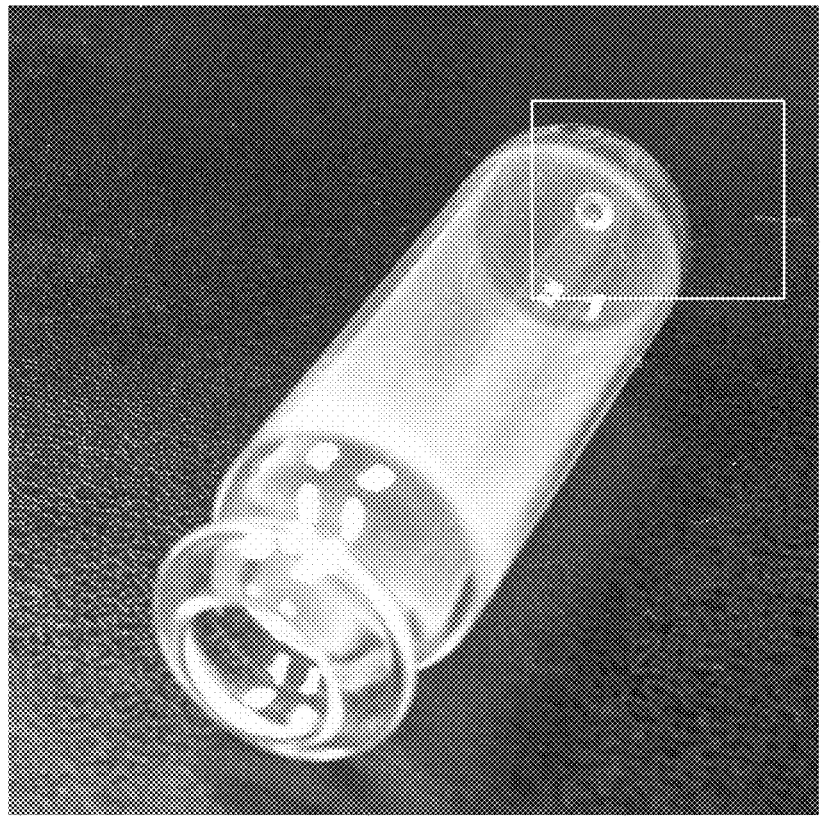
FIG. 4 is a photograph of a quartz glass container of a Comparative Example.
Figure 5:
FIG. 5 is a close up of the section enclosed in the box in FIG. 4.

Tests were performed using a conventional approach to tubular vial forming. The test was aimed at producing 2 ml vials using a standard rotary-index based, vertically-oriented, tubular-vial manufacturing machine that was developed for borosilicate vials, although some minor alterations were made to the gas burner units in order to accommodate the higher required working temperatures of fused quartz glass. The input to the process was 16 mm fused quartz tubes, approximately 1 m in length. The equipment was running at a rate sufficient to produce approximately 30 vials a minute (1800 vials per hour). FIGS. 4 and 5 show a vial made by this process. As shown in the FIGS. 4 and 5, the containers have a white/frosty appearance. This is evidence of prominent and extremely numerous surface features on both the interior and exterior of the vial. As such, the number of features in the region of interest are too numerous too count.

Figure 6:
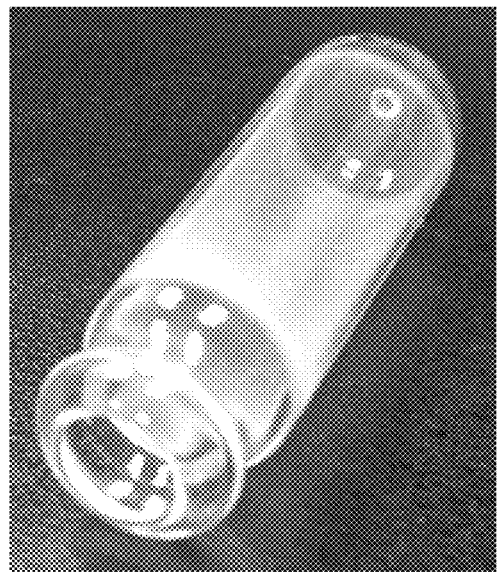
FIG. 6 is a comparison of (a) the quartz glass container formed under the Comparative Example with (b) a quartz glass container formed in accordance with a method of the present disclosure.
Figure 6:
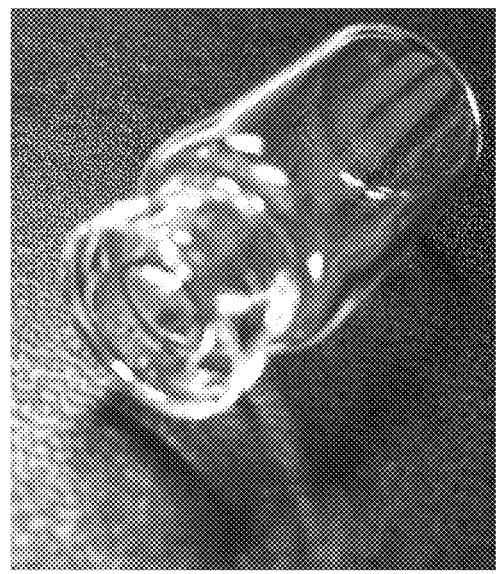

FIG. 6 compares the vial of the Comparative Example (FIG. 6(*a*)) with a vial made in accordance with the present method (FIG. 6(*b*)). The vial of FIG. 6(*b*) is substantially more clear in appearance due to the low surface features.

The foregoing description identifies various, non-limiting embodiments of a pharmaceutical container and methods of making the same. Modifications may occur to those skilled in the art and to those who may make and use the invention. The disclosed embodiments are merely for illustrative purposes and not intended to limit the scope of the invention or the subject matter set forth in the claims.

What is claimed is:

1. A quartz glass pharmaceutical container defining an interior volume and having an upper end, a base end, at least one wall defining an inner surface and an outer surface, wherein the inner surface of the container has a surface feature density of 50 or fewer surface features per square centimeter within a 1 cm band centered 1 cm from the base end of the pharmaceutical container, the surface features having a size of 1 to 200 μm.

2. The quartz glass container of claim 1, wherein the surface feature density is 10 or fewer surface features per square centimeter.

3. The quartz glass container of claim 1, wherein the surface feature density is 5 or fewer surface features per square centimeter.

4. The quartz glass container of claim 1, wherein the container has a surface feature density of 5 or fewer surface features of 50 micron or greater per square centimeter.

5. The quartz glass container of claim 1, wherein the container has a surface feature density 5 or fewer surface features of 10 micron or greater per square centimeter.

6. The quartz glass container of claim 1, wherein the quartz glass container is chosen from a vial, a tube, a vacuum sealed tube, a cartridge, a syringe, a syringe barrel, or an ampoule.

7. The quartz glass container of claim 1 comprising a pharmaceutical fluid disposed in the container.

8. A process for forming a plurality of quartz glass containers comprising:
 providing a quartz glass tube having a first open end and second open end opposite the first open end;
 forming one or more features of a container at the first open end;
 forming one or more features of a container at the second open end;
 separating the quartz glass tube at a point distal to each of the first and second open ends, the separating operation providing two containers and forming a bottom of each container, wherein the pharmaceutical packaging container defines an interior volume and having an upper end, a base end, at least one wall defining an inner surface and an outer surface, wherein the inner surface of the container has a surface feature density of 50 or fewer surface features per square centimeter within a 1 cm band centered 1 cm from the base end of the pharmaceutical container, the surface features having a size of 1 to 200 μm.

9. The process of claim 8 comprising purging the tube with a gas during the step of (i) forming one or more features of a container at the first open end, (ii) forming one or more features of a container at the second open end, or both (i) and (ii).

10. The process of claim 8, wherein the process is operated to process 50 to 3000 quartz glass tubes per hour.

11. A pharmaceutical packaging container made from the process of claim 8.

* * * * *